United States Patent [19]

Ejzak

[11] 4,277,438
[45] Jul. 7, 1981

[54] METHOD AND APPARATUS FOR MEASURING THE AMOUNT OF CARBON AND OTHER ORGANICS IN AN AQUEOUS SOLUTION

[75] Inventor: Edward M. Ejzak, Friendswood, Tex.

[73] Assignee: Astro Resources Corporation, League City, Tex.

[21] Appl. No.: 72,424

[22] Filed: Sep. 4, 1979

[51] Int. Cl.³ .................. G01N 31/12; B01J 19/08
[52] U.S. Cl. .................. 422/80; 23/230 PC; 250/436; 422/186
[58] Field of Search ............... 23/23 PC; 422/78–80, 422/189, 193, 186; 250/436

[56] References Cited

U.S. PATENT DOCUMENTS

| | | | |
|---|---|---|---|
| 3,287,088 | 11/1966 | Seevers | 23/230 |
| 3,535,087 | 10/1970 | Hart et al. | 422/50 |
| 3,854,877 | 12/1974 | Csaky | 23/230 PC |
| 3,958,941 | 5/1976 | Regan | 422/80 |
| 4,099,926 | 7/1978 | Gatlhuber | 422/193 |
| 4,124,660 | 11/1978 | Sterlini | 422/189 X |
| 4,172,116 | 10/1979 | Spevack | 422/189 X |

OTHER PUBLICATIONS

Ionics Inc. Process 5000 Series.
Org. Carbon Det. with Accuracy Simplicity & Economy, Sybron/Barnstead 1978.
Takahashi, Ultra Low Levels Toc. Analysis of Potable Water, 1976.
Goulden et al., Kinetics of Uncatalyzed Peroxydisulfate Oxidation of Org. Mat. in Fresh Water, 1978.
Goossan et al., Det. of Phosphates in Natural & Waste Waters After Photo–Chemical Decomp. & Acid Hydrolysis of Org. Phosphorous Cads. 1978.
Dissolved Organic Carbon in Plant Effluent Technicon Ind. Systems, 1977.
Envirotech Dohrman–Environmental Analyzers, 1977.
Fisher, Tracing Organics in High Purity Water Systems, 1977.
O.I. Corp. The "New Total Carbon Systems".

Primary Examiner—Michael S. Marcus
Attorney, Agent, or Firm—Arnold, White & Durkee

[57] ABSTRACT

A method and apparatus for measuring the amount of carbon and other organics in an aqueous solution is disclosed. A novel multistage reactor employs ultraviolet radiation to promote oxidation of a test sample. Oxygen and an oxidizing agent such as sodium persulfate are introduced into the solution prior to irradiation. The mixture is brought into direct contact with an ultraviolet lamp in each stage of the reactor. The design of the multistage reactor permits the desired chemical reaction to be optimized over interferring reactions.

An inorganic carbon scrubber assembly is also disclosed for operation in a total organic carbon mode.

7 Claims, 4 Drawing Figures

METHOD AND APPARATUS FOR MEASURING THE AMOUNT OF CARBON AND OTHER ORGANICS IN AN AQUEOUS SOLUTION

BACKGROUND OF THE INVENTION

This invention relates generally to a novel method and apparatus for measuring the amount of carbon and other organics in an aqueous solution. More particularly, this invention concerns a novel multistage reactor and method for irradiating an aqueous solution with ultraviolet radiation. Oxygen is introduced into the solution; and the solution and oxygen are brought into direct contact with an ultraviolet lamp in each stage of the reactor. The solution enters the lower portion of the reactor stages and exits the upper portion of each stage. The multistage reactor provides a facility for optimizing a desired chemical reaction out of several competing reactions, while reducing interferance from unwanted reactions. Testing need not be done on a batch basis; processing may proceed on a continuous basis.

In the past, it has been common to require a combustion step at high temperatures. Measurements have been performed by introducing a sample and air or oxygen at a measured rate into a metal reactor, or a quartz tube filled with a catalyst, which is running at a temperature typically between 760° C. and 900° C. Carbon in the sample is oxidized to carbon dioxide and then passed through a condenser to remove water from the system. The gas is then passed to a conventional carbon dioxide detector.

Such prior art high temperature methods have proven to be unsatisfactory because of the long response times required. Such prior art methods have proven to be extremely slow and combersome. Such methods are also succeptible to catalyst poisoning, and are generally incapable of adequately handling salts in solution in the sample to be tested.

Batch systems employing ultraviolet radiation to oxidize carbon in a sample solution are known.

One such system is disclosed in U.S. Pat. No. 3,958,941, issued May 25, 1976, to Michael Daniel Regan. Regan discloses an ultraviolet lamp 3 internal to a single stage irradiation chamber 1. Regan requires the carrier water to be absolutely pure. The Regan device requires a time consuming special cleaning cycle during which water valve 25 is opened to allow the carrier water to be circulated through a mixed bed ion exchange cartridge 27 to remove ions which might interfere with the desired reactions. After the cleaning cycle, the valve 25 is closed. A known volumn of sample, typically one milliliter, is introduced into a first water loop 9 via a sample input port 35.

An air loop 31 passes air through the top of the irradiation chamber 1. Regan also teaches that water and air is to be pumped into the top of the irradiation chamber 1, and that the water should exit through the lower portion of the irradiation chamber 1. Regan teaches that the air loop 31 is to isolate non-gaseous substances contained within the sample from the measuring chamber 11.

The Regan device is unsatisfactory and slow in that it requires a preliminary cleaning cycle to insure that the water is absolutely pure. The Regan single stage irradiation chamber is incapable of optimizing the desired reactions in order to overcome interference from undesired reactions. The Regan device is limited to batch testing, and is incapable of continuously processing sample solutions. Regan also does not appreciate, and fails to teach or suggest, that oxygen should be introduced into the sample prior to ultraviolet irradiation, and that the oxygen and water mixture should be introduced into the lower portion of the reactor in order to realize certain advantages, as set forth more fully below.

The problems enumerated in the foregoing with respect to the above prior art systems are not intended to be exhaustive, but rather are among many which tend to impair the effectiveness of previously known devices and methods for measuring organics in an aqueous solution. Other noteworthy problems may exist; however, those presented above should be sufficient to demonstrate that devices and methods for measuring organics in an aqueous solution appearing in the prior art have not been altogether satisfactory.

SUMMARY OF A PREFERRED EMBODIMENT OF THE INVENTION

Recognizing the need for an improved method and apparatus for measuring organics in an aqueous solution, it is, therefore, a general feature of the present invention of providing a novel method and apparatus which minimizes or reduces the problems of the type previously noted.

A more particular feature of the present invention resides in the provision of a multistage reactor. A feature resulting from the multistage reactor design is the ability to optimize desired reactions and simultaneously minimize interference from undesired reactions. As a correlated feature, the present invention has a relatively high tolerance for salts and other interfering ions that typically disrupt prior art devices.

A further feature pertains to the relatively fast reaction times achieved by the present invention. A collateral feature involves the introduction of oxygen into the sample before the sample is passed through the reactor and exposed to ultraviolet radiation in order to enhance the oxidation of organics in solution while simultaneously scrubbing carbon dioxide produced by the ultraviolet irradiation out of solution for detection and measurement.

A still further feature involves the ability of the present invention to continuously process a test solution without being limited to batch processing. This also permits the feature of continuous monitoring capability. The present invention can include the additional feature of an alarm mechanism that actuates when the level of organics deviates beyond a predetermined threshold or outside a predetermined range.

An invention for measuring carbon and other organics in an aqueous solution according to a presently preferred embodiment intended to substantially incorporate the foregoing features includes means for introducing oxygen into the sample, then irradiating the sample the oxygen mixture with ultraviolet radiation in a multistage reactor constructed in accordance with the present invention to optimize desired reactions while minimizing interference. A detector then detects the resultant carbon dioxide, or other desired organics.

An oxidizing agent such as sodium peroxydisulfate is introduced prior to irradiation to enhance oxidation. A gas-liquid separator removes the liquid. An acid mist eliminator, coalescer and particle filter process the gas before it goes to the detector.

The multistage reactor preferably comprises three reactor stages, each having an input aperature at the bottom of the stage and an output aperature near the top of the stage. Each stage comprises a generally cylindrical housing formed around an ultraviolet lamp at least partly interior to the housing. The solution-oxygen mixture thus flows upwardly through an annular sample space and directly contacts the ultraviolet lamp. As a result, the oxygen added prior to irradiation enhances oxidation and simultaneously functions as a scrubber or carrier gas. The stages are connected in series so that the solution passes through each stage successively.

Reactor connection tubes connect the various stages of the multistage reactor together. While the solution-oxygen mixture is passing through the reactor connection tubes between stages, the oxygen in the mixture assists in reversing certain interference reactions.

Examples of the more important features of this invention have thus been outlined rather broadly in order that the detailed description thereof that follows may be better understood, and in order that the contribution to the art may be better appreciated. There are, of course, additional features of the invention that will be described hereinafter and which will also form the subject of the claims appended hereto. These features of the present invention will become apparent with reference to the following detailed description of a presently preferred embodiment thereof in connection with the accompanying drawings, wherein like reference numerals have been applied to like elements, in which:

DETAILED DESCRIPTION OF A PREFERRED EMBODIMENT OF THE INVENTION

Irradiation of organic compounds dissolved in water with ultraviolet radiation in the presence of oxygen results in oxidation of the organics, thus facilitating detection of the organics. Interference from other substances also dissolved in the water has long plagued prior art methods of measuring such organics. A method and apparatus that does not require additional cleaning and separation apparatus, which is capable of optimizing the desired reactions to reduce interference, which has a wide range of measurement, which is capable of optimizing the desired reactions to reduce interference, which has a fast reaction time, and which is capable of continuous processing is needed.

Figure 1:
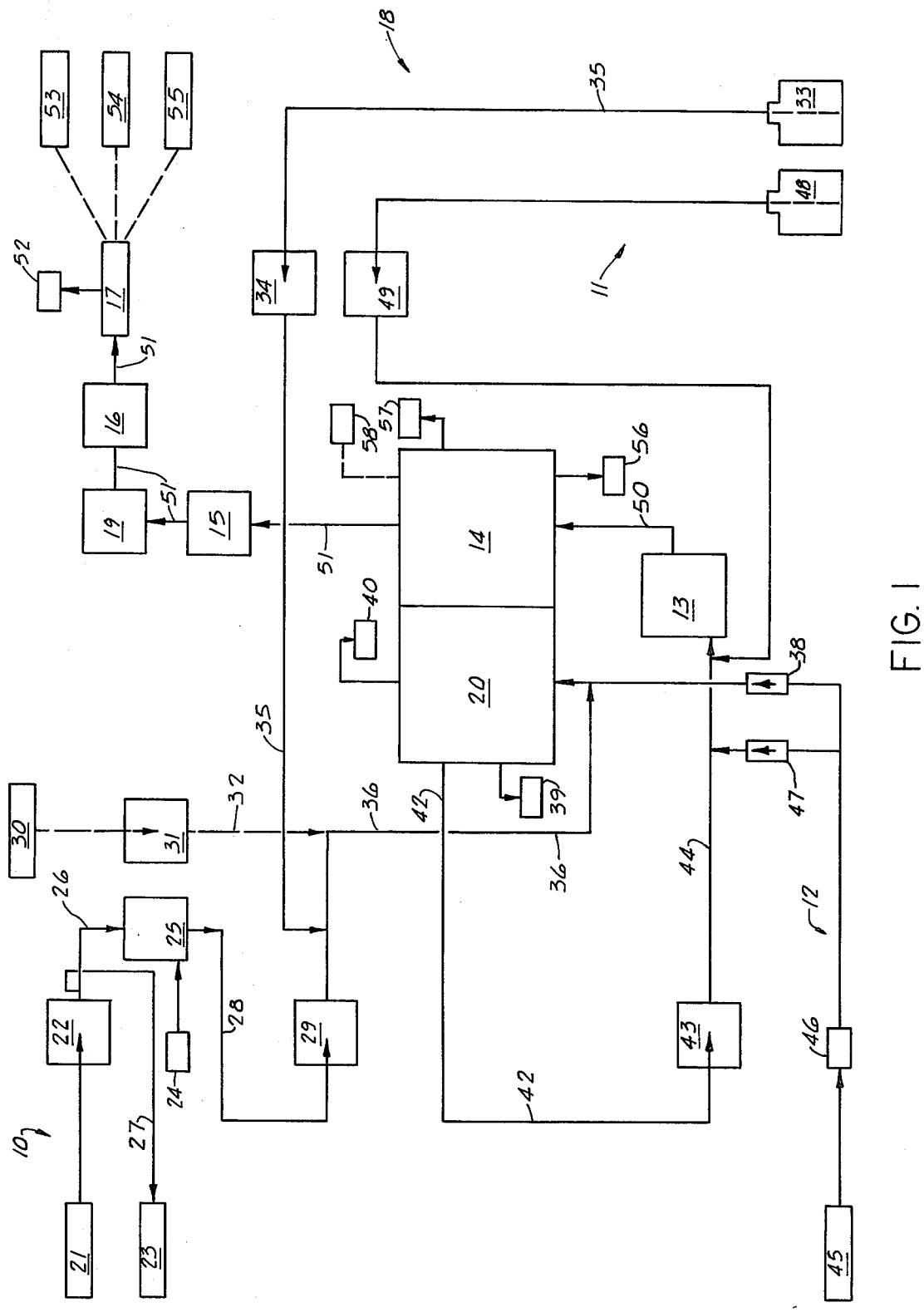
FIG. 1 is a block diagram depicting an embodiment of the present invention.

Turning first to FIG. 1, there is shown a presently preferred embodiment of the invention comprising input means 10 for introducing a sample, first means 11 for introducing persulfate ions into the sample, second means 12 for introducing oxygen into the sample, a multistage reactor 13, a gas-liquid separator 14, a particle filter 16, and a detector 17.

Sample water enters input means 10, and flows toward the multistage reactor 13. Persulfate ions are introduced into the sample water by first means 11. Oxygen is introduced into the sample water by second means 12. Thus, before the sample water enters the multistage reactor 13, persulfate ions and oxygen are mixed with the sample water.

In the multistage reactor 13, the sample water is exposed to ultraviolet radiation. The gas and liquid mixture then flows to the gas-liquid separator 14 where the water and other liquid components are removed.

The separated gas passes through the particle filter 16, and is then fed to the detector 17. The detector 17 detects and measures the organics of interest.

If the detector 17 is an infrared detector and uses a noble metal as a reflector, an acid mist eliminator 15 should follow the gas-liquid separator 14 in order to filter acidic mist from the gaseous mixture before it goes to the detector 17.

It is desirable that the invention have a total organic carbon mode. In the total organic carbon mode, the water sample flows through a standard inorganic carbon scrubber assembly 20 before the water sample flows to the multistage reactor 13. The standard inorganic carbon scrubber assembly 20 removes inorganic carbon from the sample water when the apparatus is in the total organic carbon mode. In the total organic carbon mode, it is desirable to introduce acid into the sample water to cause inorganic carbons to become insoluble when carbon dioxide is formed. Such carbon dioxide is then removed by the inorganic carbon scrubber assembly 20. In the present instance, this is essentially accomplished by third means 18 for introducing acid into the water sample.

In the total carbon mode, the water sample may bypass the standard inorganic carbon scrubber assembly 20 and flow directly to the multistage reactor 13; that is, input means 10 may be connected directly to the multistage reactor 13.

In a preferred embodiment, input means 10 comprises an input port 21 adapted to receive a gross sample input. A first pump 22 forces the sample fluid to flow through the apparatus. In practice, a first pump 22 flow rate of 28 cc per minute has given satisfactory results. Excess sample fluid may be drawn off and expunged through a first drain 23.

A manual sample or calibrate inlet 24 may also be provided, along with a second valve 25. The gross sample input flows through a first tube, pipe or conduit 26 to a second valve 25, while excess sample fluid is drawn off through a second tube 27 to a first drain 23. The remaining sample fluid flows through a third tube 28 to a second pump 29. In practice, the second pump 29 may be set at a flow rate between 0.3 to 16 cc per minute; and such flow rates have given satisfactory results in practice.

It is often desirable to dilute the sample fluid.

For example, when the sample fluid has a relatively large salt content, dilution of the sample may reduce interference from the salt ions. In the present instance, this is essentially accomplished by dilution water input 30 and a third pump 31. The third pump 31 may be used to pump dilution water through a fourth tube 32 to be mixed with the sample fluid. Preferably, water used for dilution should be pure distilled water free of any organic or carbon contaminants.

It will be appreciated that the range of the apparatus may be extended to conveniently measure high concentrations of organics in solution by dilution of the sample fluid.

In the total organic carbon mode, the fluid mixture flows through a sixth tube 36 into the standard inorganic carbon scrubber assembly 20. Preferably, oxygen is mixed with the sample fluid before the fluid is introduced into the standard inorganic carbon scrubber assembly 20. A first flow controller 38 controls the amount of oxygen mixed with the sample fluid. A flow rate of 150 cc of oxygen per minute has given satisfactory results in practice. The ratio of the oxygen flow rate through the first flow controller 38 to the sample fluid flow rate through the second pump 29 is important. Typical flow rates through the second pump 29 may range between 0.3 and 16 cc per minute. Thus an oxygen flow rate between 18¾ and 500 times the flow rate of the sample fluid should be maintained.

Third means 18 preferably comprises an acid reservoir 33, a fourth pump 34 and a fifth tube 35. Preferably, phosphoric acid, typically 20 volume percent, is pumped from the acid reservoir 33 and through the fifth tube 35 by the fourth pump 34 and mixed with the sample fluid. Preferably, the pH of the sample water should be lowered to a point near a pH of 2. In practice, acid flow rates between 0.12 and 1.05 cc per minute have given satisfactory results.

The phosphoric acid and dilution water, if any, may be mixed with the sample fluid in a sixth tube 36, where the mixture then flows to the inorganic scrubber assembly 20.

The standard inorganic carbon scrubber assembly 20 removes inorganic carbon from the sample fluid. By-product fluid is expelled through a drain 39, and by-product gas is expelled through a vent 40. The remaining fluid exits through a ninth tube 42 to the fifth pump 43.

For operation in the total carbon mode, the tube 42 is directly connected to the second valve 25, thus isolating the standard inorganic carbon scrubber assembly 20 from the remainder of the apparatus such that the fluid flows directly from the second valve 25 to the ninth tube 42.

Inorganic carbon typically encountered in practice is most often in the form of carbonates. This inorganic carbon can be removed by introducing oxygen into the sample fluid and making the sample fluid acidic. Thus, the apparatus alternatively may be utilized in the total carbon mode by discontinuing the flow of oxygen through the first flow controller 38 and by discontinuing the flow of acid through the fourth pump 34. In such an event, the standard inorganic carbon scrubber assembly 20 would be rendered substantially inoperative.

A fifth pump 43 pumps the sample fluid at a rate of typically 0.12 and 14 cc per minute. The sample fluid passes through a tenth tube 44 to the multistage reactor 13. Before reaching the multistage reactor 13, oxygen and persulfate ions are mixed with the sample fluid.

In a preferred embodiment, second means 12 comprises an oxygen reservoir 45, a pressure regulator 46 and a second gas flow controller 47. In practice, settings of approximately 15 pounds per square inch for the pressure regulator 46 have given satisfactory results. Flow rates between 15 and 200 cc per minute of oxygen through the second gas flow controller 47 have given satisfactory results in practice. Under certain conditions, air may be substituted for pure oxygen in second means 12.

The ratio of the flow rate of oxygen through the second flow controller 47 and the flow rate of sample through the fifth pump 43 is critical to achieve a preferred operation of the apparatus. A ratio greater than 1 should always be maintained. For sample fluid flow rates as great as 14 cc per minute through the fifth pump 43, the minimum oxygen flow rate should be about 15 cc per minute. The oxygen flow rate could be as much as 200 cc per minute. In practice, ratios greater than 1:1 and less than 1667:1 may be used with utility. Typically, ratios on the order of 15:1 should be satisfactory.

First means 11 preferably comprises a persulfate reservoir 48 and a sixth pump 49. In practice, the sixth pump 49 may pump at a rate of between 0.12 to 1.05 cc per minute. Preferably, the persulfate reservoir 48 should contain sodium peroxydisulfate ($Na_2S_2O_8$). In practice, a one molar solution has given satisfactory results.

The sample mixture is exposed to ultraviolet radiation in the multistage reactor 13, as explained more fully below. The solution then passes through an eleventh tube 50 to the gas liquid separater 14. In a preferred embodiment, the gas liquid separater 14 also includes a constant head pressure assembly to maintain the pressure of the gas exiting through a twelfth tube 51.

In the case of carbon analysis, carbon dioxide exits through the twelfth tube 51. The carbon dioxide is passed through the acid mist eliminator 15. The carbon dioxide gas also passes through a coalescer 19 and the particle filter 16 to the detector 17. In a preferred embodiment, the coalescer 19 may also include a salt collector. Preferably, the detector 17 comprises an infrared carbon dioxide analyzer. The carbon dioxide and other gasses are then expelled through a vent 52.

The acid mist eliminator 15 may be unnecessary for detectors 17 that are not damaged by acid. Infrared detectors 17 that use noble metals for reflectors, however, require an acid mist eliminator 15. The coalescer 19 is utilized to remove entrained water that would otherwise tend to condense out. The coalescer 19 insures that the gas going to the detector 17 is truely gaseous. Short staple ceramic fiber material gives satisfactory results in the coalescer 19.

The detector 17 may be used to drive front panel outputs 53, such as meters, panel lights and other conventional monitoring devices. The detector 17 may also be used to drive recorders and alarms 54. Because the invention is capable of processing sample fluid on a continuous basis, the alarms 54 may be used to sound an alert when the level of organics in the sample exceeds a predetermined range.

The detector 17 may also provide digital output data to printers and computers 55 for analysis in accordance with conventional techniques.

Figure 2:
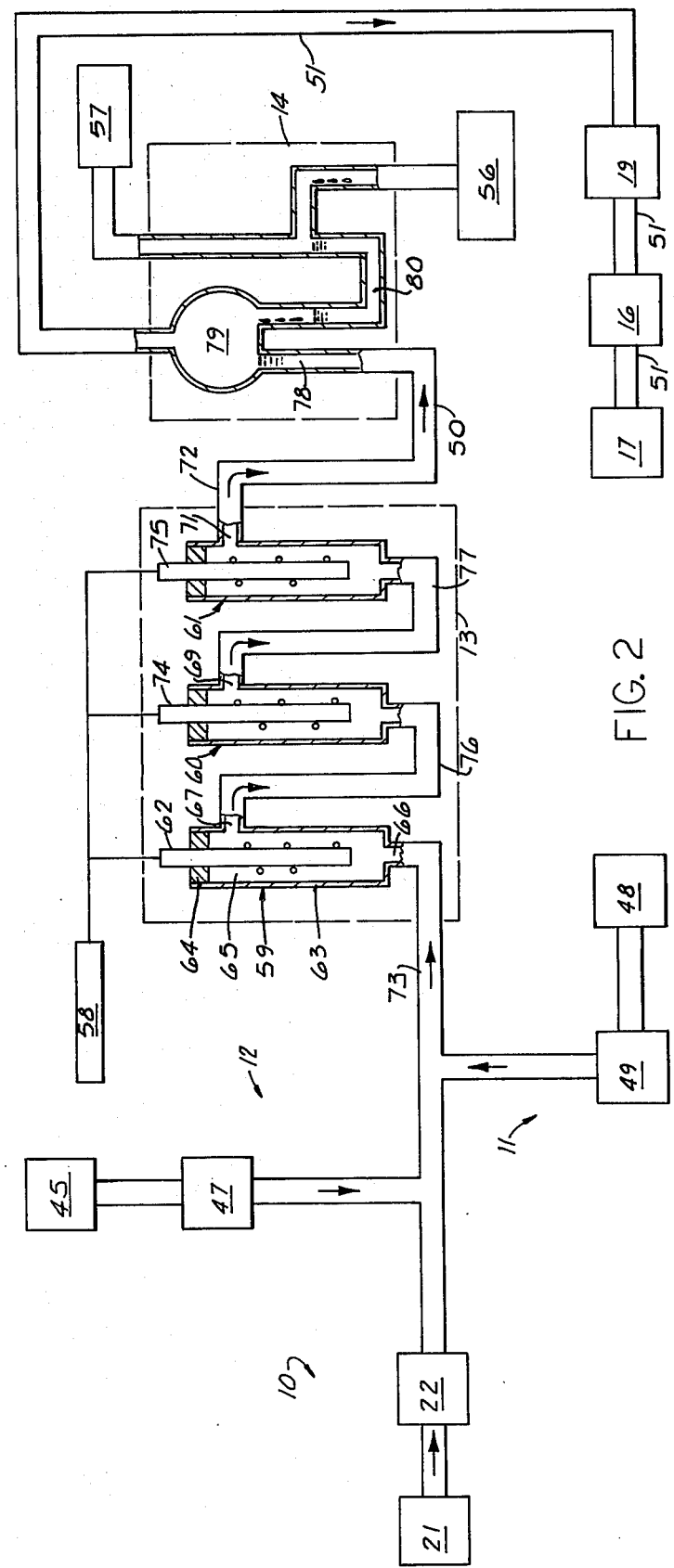
FIG. 2 is a block diagram in partial cross section showing the multistage reactor in more detail.

Referring to FIG. 2, the multistage reactor 13 is illustrated in more detail.

In a preferred embodiment, the multistage reactor 13 has three substantially identical stages: a first stage 59, a second stage 60 and a third stage 61. The first stage 59 has a first housing 63 that is generally cylindrical in shape. The first housing 63 has a first ultraviolet lamp 62 inserted therein and which is at least partly interior to the first housing 63. A first seal 64 sealingly engages the first lamp 62 to provide an airtight and fluid-tight enclosure. Thus, a first sample space 65 is formed in the first stage 59.

Figure 3:
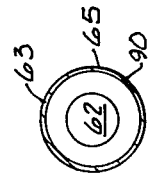
FIG. 3 is a cross-sectional view of one stage of the multistage reactor showing the annular sample space.

As best shown in FIG. 3, the sample space 65 has a generally annular cross-section. In a preferred embodiment, the annular sample space 65 has a cross-sectional thickness approximately less than 3.2 millimeters between the lamp 62 and the inside wall of the housing 63. Preferably, the lamp 62 has about a nine millimeter diameter and the housing 63 has about an eleven millimeter diameter, leaving a sample thickness of about one millimeter.

The first stage 59 has a first input aperture 66 and a first output aperture 67. The first input aperture 66 is preferably placed near the bottom of the first stage 59. The first output aperture 67 is preferably placed near the top of the first stage 59. This arrangement achieves a significant advantage in improving the reaction time, efficiency and effectiveness of the oxidation taking place in the first reactor 59.

Second means 12 introduces oxygen into the mixture before it enters the first stage 59. The sample fluid enters the sample space 65 and is allowed to directly contact the ultraviolet lamp 62. The ultraviolet radiation from the lamp 62 generates ozone when it irradiates the oxygen, which enhances the oxidation of the sample fluid. In addition, the persulfate ions will oxidize carbon or other organics in the sample fluid. The oxygen previously introduced into the sample mixture will tend to bubble upwards through the sample space 65 and act as a carrier gas to remove carbon dioxide or other gasses produced by the oxidation reaction. The persulfate ions in solution tend to result in a pH of the solution approaching zero. Carbon dioxide is less soluble in such an acidic solution and it tends to bubble out quickly.

The second stage 60 and the third stage 61 are constructed substantially in accordance with the construction of the first stage 59. The second input aperture 68 of the second stage 60 is connected to the first output aperture 67 of the first stage 59. Similarly, the second output aperture 69 of the second stage 60 is connected to the third input aperture 70 of the third stage 61.

In the illustrated embodiment, the first input aperture 66 is connected to a reactor input 73. The third output aperture 71 is connected to a reactor output 72. Thus, the stages of the multistage reactor 13 are connected in series such that the sample fluid flows through each stage successively.

A conventional high voltage electrical source 58 may be used to power the ultraviolet lamps 62, 74 and 75.

If desired, the third stage 61 may be eliminated and only two stages 59 and 60 utilized for oxidation. Alternatively, more than three stages may be used in the multistage reactor 13. Preferably, a minimum of three stages are required.

Elimination of interference from salts and other undesired reactions has long been a problem plaguing prior art devices. Interference may result from the presence of any halogen ion, such as chlorine, fluorine, bromine, iodine, etc. For example, in the presence of sodium chloride, or common table salt, dissolved in the water sample or found in sea water, the chlorination of carbon will interfere with the desired oxidation of carbon. Because of the multistage configuration of the reactor 13, the desired oxidation process may be emphasized. Ultraviolet radiation tends to enhance chlorination of the carbon. However, when the sample mixture passes out of the output aperture 67 of the first stage 59, the oxygen present in the mixture will tend to reverse the chlorination reaction. Moreover, even in the absence of ultraviolet radiation in first reactor connecting tube 76 connecting the output aperture 67 to the input aperture 68, the persulfate ions tend to continue the oxidation process during the time the chlorination reaction is reversing.

As the sample mixture enters the second stage 60, ultraviolet radiation from the second lamp 74 begins the chlorinization interference reaction again, while simultaneously enhancing the oxidation reaction. Again, as the sample passes out the second output aperture 69 and into second reactor connecting tube 77, the chlorination reaction reverses again while the oxidation reaction continues. This cycle is repeated as the sample is passed through succeeding stages of the multistage reactor 13. Thus, the chlorination interference may be reduced or minimized while the oxidation reaction is enhanced. Moreover, the multistage reactor 13 permits the optimization to take place in a continuous processing environment so that sample fluid may be continuously processed without stopping the apparatus. The disadvantages of batch processing are avoided.

While the above discussion has been specifically with reference to carbon and interference from chlorine, it will be understood that the discussion also applies to interference from any other halogens; and the operation of the apparatus in such cases is substantially equivalent. Additionally, the discussion applies equally to any organic or other chemical sought to be analyzed, in addition to carbon.

The mixture then flows through the eleventh tube 50 to the gas liquid separator and constant head pressure assembly 14. The gas liquid separator and constant head pressure assembly 14 preferably has an output column 78. Gas in the sample mixture is allowed to bubble into a gas collecting chamber 79, while the fluid drains into a head pressure assembly 80 and is expelled through the drain 56. Waste gas is exhausted through the vent 57. Carbon dioxide resulting from the oxidation reaction then passes through the twelfth tube 51 to the acid mist eliminator 15, the coalescer and salt collector 19 and the particle filter 16. The carbon dioxide may then be detected by the conventional detector 17, preferably in infrared carbon dioxide analyzer.

In a preferred embodiment, sodium peroxydisulfate 48 is used as a source for persulfate ions. Persulfate ions have a high electromotive force and have been found particularly suitable for oxidation of organics. Ammonium persulfate may also be used, but appears to be less satisfactory because it tends to interfere with the detection of organics in the presence of salts. Potassium persulfate may be used, but has generally proven to be less satisfactory because of its low solubility in water. The ratio of persulfate ions to carbon should preferably be on the order of 5 to 1 in the absence of any salt interference. With salt present in the sample mixture, the persulfate ion to carbon ratio should be increased to somewhere on the order of 15 to 1, or higher, to assure the presence of sufficient persulfate ions to react with the carbon in solution. The salt ions combine with the persulfate ions, thus creating an additional "demand" for the persulfate ions. The increased persulfate ion to carbon ratio insures that sufficient persulfate ions remain after the sale interference to oxidize the chemical of interest (here carbon). Dilution of the sample may sometimes be required where salts are present to reduce interference from salt ions.

In a preferred embodiment, the housing 63 of the reactor stages 59, 60 and 61 is formed from quartz. Quartz is preferred because it is relatively transparent to ultraviolet light and transmits such light with relatively negligible attenuation. In a preferred construction, the quartz housing 63 is coated with an ultraviolet reflective media 90, as shown in FIG. 3. The operation of the reactor stages 59, 60 and 61 is enhanced by the multiple reflections that occur from the reflective media 90, causing the ultraviolet radiation to be reflected back into the stage 59, 60 or 61. In practice, aluminum foil has given satisfactory results as the ultraviolet reflective media 90.

In a preferred construction, the multiplestage reactor 13 is encased in a thermal isolation medium (not shown), such as polyurethane foam or equivalent material. The thermal isolation medium generally assists in maintaining a relatively constant temperature within the multiplestage reactor 13 at thermal equilibrium.

Preferably, mossy tin is used in the acid mist eliminator 15. The acid introduced by third means 18 should preferably be phosphoric acid ($H_3PO_4$).

It is generally believed, that for best results, a minimum of three stages should be used in the multistage reactor 13. Fifteen watt mercury-type ultraviolet lamps have given satisfactory results in practice for the lamps 62, 74 and 75. In a preferred embodiment, the lamps 62, 74 and 75 may be about 7 inches long.

Other conventional detectors 17 may be used in the place of the preferred infrared carbon dioxide analyzer. For example, coulometric or conductivity detectors may be used to detect carbon dioxide. Preferably, the infrared carbon dioxide analyzer 17 should not use noble metals to reflect the infrared radiation to the detector.

Other organics may be detected with the disclosed apparatus by substituting appropriate detectors for the detector 17. The pumps 22 and 49 are preferably peristaltic pumps.

Figure 4:
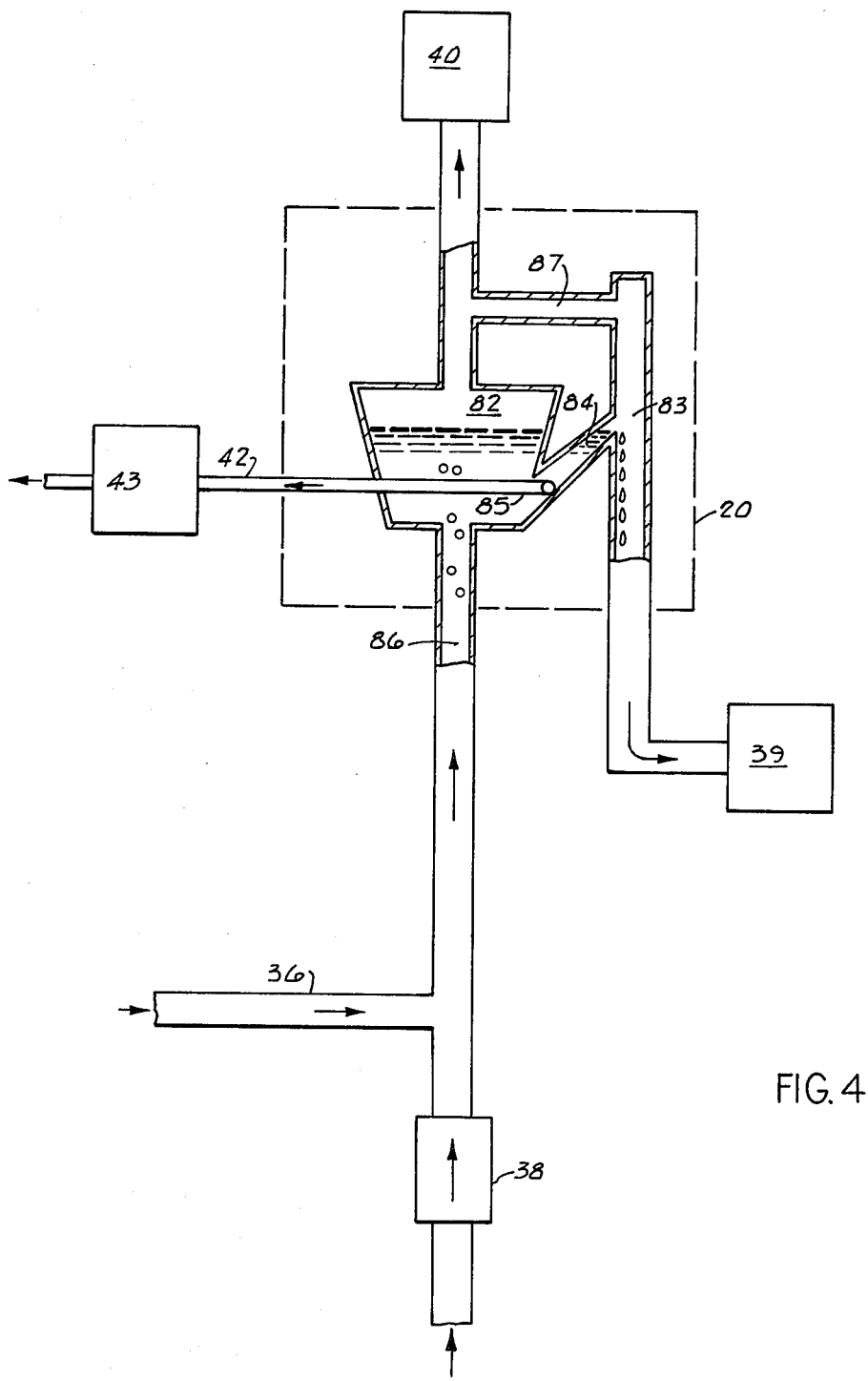
FIG. 4 is a partial cross-sectional view showing the standard inorganic carbon scrubber assembly in more detail.

Referring to FIG. 4, the standard inorganic carbon scrubber assembly 20 is illustrated in more detail. Oxygen from the first flow controller 38 is mixed with the sample water-acid mixture flowing through the sixth tube 36. The water-acid-oxygen mixture then enters a scrubber column 86. Carbon dioxide is formed which is relatively insoluble in the acidic water; hence it bubbles out. The carbon dioxide exits through a scrubber collecting chamber 82 to the vent 40.

The liquid sample collects in the bottom of the chamber 82 and an upwardly sloped drain channel or tube 84. Excess liquid flows into a drain column 83 and exits to the drain 39. A pressure equalizing channel 87 equalizes the pressure between the chamber 82 and the drain column 83.

A resample tube 85 extends into the drain channel 84 and sample liquid is drawn away through the ninth tube 42 to the fifth pump 43.

It will be understood that other scrubber assemblies of a conventional type may be substituted for the standard inorganic scrubber assembly 20.

SUMMARY OF THE ADVANTAGES OF THE INVENTION

It will be appreciated that in constructing an apparatus for measuring the amount of carbon and other organics in an aqueous solution according to the present invention, certain significant advantages are provided.

In particular, a multistage reactor is provided which can optimize the desired oxidation reactions while simultaneously minimizing interference from undesired salts or halogens. As a consequence, the present invention has a relatively high tolerance for salt and other interfering ions; and measurements are not disrupted by the presence of salts.

By introducing oxygen into the sample fluid before the sample has passed through the stages of the multistage reactor, the present invention achieves the advantage of utilizing the oxygen so introduced both as an aid to oxidation, as an agent to reverse the interference from salts, and also as a scrubbing agent or carrier gas to carry away carbon dioxide produced during oxidation. The sample is fed through each stage of the reactor from bottom to top in order to enhance the scrubbing action of the carrier gas and improve the reaction time of the invention.

The present invention has the advantage of being able to continuously process a test solution. A resulting advantage derived from continuous processing is that the invention is capable of sounding an alarm as soon as the level of organics in the test solution deviates beyond a predetermined range.

The present invention has the advantage of not requiring extended warm up periods. The present invention does not have problems of catalyst poisoning, and does not require high temperatures for operation. By avoiding high temperatures, the invention has the advantage of avoiding the reactor failures that commonly occur because salts have a high vapor pressure at high temperatures and tend to attack the walls of conventional reactors and thus weaken them. By avoiding high temperatures, the present invention has the further advantage of avoiding thermal shock problems.

The present invention also achieves the advantage of significant efficiency in operation.

The present invention has a final advantage of being adapted for the measurement of organics in an aqueous solution without requiring cumbersome or highly sophisticated and expensive equipment. Highly purified water and gasses are not required in order to make accurate measurements. Additional cleaning and separation apparatus is not required.

Further modifications and alternative embodiments of the apparatus of this invention will be apparent to those skilled in the art in view of this description. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes may be made in the shape, size and arrangment of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. An apparatus for measuring the amount of oxidizable chemicals in a solution, comprising:
    first means for supplying a test solution
    second means connected to said first means for introducing an oxidizer into the test solution;
    means defining a source of oxygen connected to and communicating with a third means, said third means introducing oxygen into the test solution, in said first means, prior to irradiation of the test solution;
    a multistage reactor, said reactor having a plurality of individual, separated stages, each of said stages having an input aperture and an output aperture, each of said stages having an ultraviolet lamp at least partly internal to said stage, said lamp being adapted to directly contact the test solution, said input apertures being lower than said output apertures to permit oxygen introduced into the test solution to scrub off insoluble gases formed by oxidation of the test sample, said input aperture of the initial said stage being in fluid communication with said first, second and third means, conduit means being connected to said output aperture of each stage and being in fluid communication with said input aperture of the succeeding said stage, said output aperture of the final said stage being in fluid communication with a reactor output; and detector means for detecting carbon dioxide, said detector means being in fluid communication with said reactor output.

2. The apparatus of claim 1, wherein said oxidizer introduced by said second means comprises a persulfate ion in solution.

3. The apparatus of claim 1, wherein said oxidizer introduced by said second means comprises sodium peroxydisulfate.

4. The apparatus of claim 1, further comprising an inorganic carbon scrubber assembly preceding said second and third means and said multistage reactor, said inorganic carbon scrubber assembly being adapted to remove inorganic carbon from the test sample prior to introduction of the test sample into said multistage reactor.

5. The apparatus of claim 1, further comprising:
gas-liquid separator means, said gas-liquid separator means being interposed between said multistage reactor and said detector means, said gas-liquid separator means being adapted to separate insoluble gases from the test sample fluid.

6. The apparatus of claim 5, wherein at least one of said stages of said multistage reactor further comprises a generally cylindrical housing coaxially centered around one of said ultraviolet lamps forming an annular sample space around said lamp.

7. The apparatus of claim 6, wherein said annular sample space has a thickness around said said lamp equal to or less than about 3.2 millimeters.

* * * * *

UNITED STATES PATENT AND TRADEMARK OFFICE
CERTIFICATE OF CORRECTION

PATENT NO. : 4,277,438
DATED : July 7, 1981
INVENTOR(S) : Edward M. Ejzak

It is certified that error appears in the above-identified patent and that said Letters Patent are hereby corrected as shown below:

Column 1, line 19, "interferance" should be --interference--.

Column 1, line 35, "combersome" should be --cumbersome--.

Column 1, line 51, "volumn" should be --volume--.

Column 3, line 2, "aperature" should be --aperture--.

Column 3, line 3, "aperature" should be --aperture--.

Column 8, line 43, "pre-" should be --per- --.

Column 8, line 56, "sale" should be --salt--.

Column 10, line 55, "solution" should be --solution;--

Column 12, line 20, "said" (second occurrence) should be deleted.

*Signed and Sealed this*

*Twenty-fourth* Day of *November 1981*

[SEAL]

Attest:

GERALD J. MOSSINGHOFF

*Attesting Officer*   *Commissioner of Patents and Trademarks*